United States Patent
Kadzimirsz et al.

(10) Patent No.: US 8,013,117 B2
(45) Date of Patent: Sep. 6, 2011

(54) SOLUTION-PHASE SYNTHESIS OF LEUPROLIDE AND ITS INTERMEDIATES

(75) Inventors: Daniel Kadzimirsz, Leuna (DE); Gerhard Jas, Leuna (DE); Volker Autze, Leuna (DE)

(73) Assignee: Nanokem S.A. (UY)

( * ) Notice: Subject to any disclaimer, the term of this patent is extended or adjusted under 35 U.S.C. 154(b) by 402 days.

(21) Appl. No.: 12/094,759

(22) PCT Filed: Nov. 21, 2006

(86) PCT No.: PCT/EP2006/011144
§ 371 (c)(1),
(2), (4) Date: Sep. 11, 2008

(87) PCT Pub. No.: WO2007/059921
PCT Pub. Date: May 31, 2007

(65) Prior Publication Data
US 2009/0005535 A1    Jan. 1, 2009

(30) Foreign Application Priority Data
Nov. 25, 2005 (EP) .................................. 05025801

(51) Int. Cl.
*C07K 7/00* (2006.01)
*C07K 7/06* (2006.01)
(52) U.S. Cl. ....................................... 530/328; 530/300
(58) Field of Classification Search .................. None
See application file for complete search history.

(56) References Cited

U.S. PATENT DOCUMENTS

| | | |
|---|---|---|
| 3,914,412 A | 10/1975 | Gendrich et al. |
| 3,972,859 A | 8/1976 | Fujino et al. |
| 4,005,063 A | 1/1977 | Gendrich et al. |
| 4,008,209 A | 2/1977 | Fujino et al. |
| 2003/0018163 A1 | 1/2003 | Eggen et al. |
| 2003/0018164 A1 | 1/2003 | Eggen et al. |

FOREIGN PATENT DOCUMENTS

| | | |
|---|---|---|
| DE | 2446005 A1 | 4/1975 |
| EP | 1 291 356 A2 | 3/2003 |

OTHER PUBLICATIONS

Definition of moiety from http://dictionary.reference.com/browse/moiety, pp. 1-3. Accessed Aug. 26, 2010.*
Definition of derivative from http://cancerweb.ncl.ac.uk/cgi-bin/omd?query=derivative, pp. 1-5. Accessed Jul. 7, 2005.*
Ivo F. Eggen, et al., "DioRaSSP: Diosynth Rapid Solution Synthesis of Peptides", "Organic Process Research & Development", 2005, pp. 98-101, vol. 9, No. 1, Publisher: American Chemical Society, Published on Web Jan. 6, 2005.
Peng Li, et al., "1-Ethyl 2-Halopyridinium Salts, Highly Efficient Coupling Reagents for Hindered Peptide Synthesis both in Solution . . . ", "Tetrahedron 56", Jul. 20, 2000, pp. 8119-8131, Publisher: Elsevier Science Ltd., Published in: CN.
Christine E. Garrett, et al., "New Observations on peptide bond formation using CDMT", "Tetrahedron Letters 43", Apr. 17, 2002, pp. 4161-4165, Publisher: Elsevier Science Ltd., Published in: US.
So-Yeop Han, et al., "Recent Development of peptide coupling reagents in organic synthesis", "Tetrahedron 60", Jan 5, 2004, pp. 2447-2467, Tetrahedron report No. 672, www.sciencedirect.com, Publisher: Elsevier Science Ltd., Published in: KR.
Pen Li et al., "Current Synthetic Approches to Peptide and Peptidomimetic Cyclization", Current Organic Chemistry, 2002, 6, pp. 411-440, Bentham Science Publishers Ltd.
M. Mergler et al., "Synthesis and Application of Fmoc-His(3-Bum)-OH", Journal of Peptide Science, J. Peptide Sci. 7: 502-510, 2001, DOI: 10.1002/psc.345, European Peptide Society and John Wilrey & Sons, Ltd.
Philip J. Kocienski, "Protecting Groups", "Edition 3—Paperback", Mar. 28, 2005, Publisher: Thieme Medical Publishers, Inc., Published in: US, Only Table of Contents provided.

* cited by examiner

*Primary Examiner* — Julie Ha
(74) *Attorney, Agent, or Firm* — DeMont & Breyer LLC

(57) ABSTRACT

A process for producing a nonapeptide leuprolide and an intermediate N-protected oligopetides, wherein at least one peptide bond of the compound is formed by reacting an activated carboxylic acid and an amine component in a continuous flow.

18 Claims, No Drawings

SOLUTION-PHASE SYNTHESIS OF LEUPROLIDE AND ITS INTERMEDIATES

This application claims the priority benefit to European Patent Application EP 05 025 801.1, filed 25 Nov. 2005, the disclosure of which is incorporated by reference in its entirety.

The present invention relates to the chemical syn-thesis of leuprolide, which is a nonapeptide of the formula:

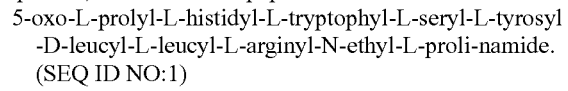
(SEQ ID NO:1)

The nonapeptide leuprolide or leuprorelin is a synthetic peptide having strong ovulation inducing activity, and is known since many years. The compound as well as derivatives thereof are described for instance in DE 2446005C2 or U.S. Pat. No. 3,914,412.

On the other hand, peptide synthesis as such is well known in the state of the art and has been further developed over the years.

However, although the synthesis of medium-large peptide for basic research is a well established procedure, the combination of the 20 proteinogenic amino acids and growing number of unnatural amino acids makes each peptide synthesis at the industrial level unique, requiring closer attention to each amino acid coupling.

In general, two different types of peptide synthesis may be distinguished, namely solution phase synthesis and solid phase synthesis. The latter has the advantage that it allows a general synthesis protocol and may easily be automated. However, one of the disadvantages is the fact that a high excess of reactants is necessary in order to allow for complete reactions, making the process as such cost-expensive. Moreover, the scale-up of solid phase synthesis processes is difficult.

On the other hand, solution phase synthesis processes allow for the work-up of intermediates. However, the more balanced ratio of starting components and reactants in classical solution phase processes goes at the cost of either reaction time or lower conversion to the desired product. Prolonged reaction time often leads to side reactions, namely epimerisation. To avoid these undesirable effects, higher dilution of the starting components and reactants is necessary, however, this usually results in longer reaction times or lower throughput.

Therefore, recent developments in peptide solution phase synthesis use an excess of one starting material, namely the activated carboxylic component, in order to ensure a rapid and complete amide bond formation, followed by the use of a scavenger in the form of an amine comprising a free anion or a latent anion for quenching excess reagent. Such processes are described for example by I. F. Eggen et al., Organic Process Research & Development 2005, 9, 98-101 and, in the US patent applications US 2003/0018163 A1 and US 2003/0018164 A1.

However, the disadvantage of these processes is the use of an excess of one starting component which makes the process less attractive for large scale synthesis because it requires high amounts of starting materials.

Accordingly, it is the object of the present invention to provide an efficient synthesis method for the preparation of leuprolide which overcomes the disadvantages of the state of the art and is applicable to produce leuprolide not only in a small scale syntheses, but in a large scale ranging from grams to even more than 100 kg.

It is a further object of the present invention to establish a synthesis method for leuprolide that avoids epimerisation and/or racemisation.

The present invention is based on the finding that the synthesis of leuprolide may be improved by using a method that provides for an efficient contact of the reaction components during the process.

Accordingly the invention relates to a process for producing the nonapeptide leuprolide wherein at least one peptide bond of the compound is formed by reacting an activated carboxylic acid and an amine component in a continuous flow.

Another aspect of the invention relates to a process for the preparation of N-protected oligopeptides, in particular the N-terminal pentapeptide and the C-terminal tetrapeptide, which are intermediates for the preparation of leuprolide, wherein at least one peptide bond of the compound is formed by reacting an activated carboxylic acid and an amine component in a continuous flow.

As a rule all amino groups of the activated carboxylic acid and all amino groups with the exception of the N-terminal amino group of the amine component will be protected by suitable amino protecting groups. These protecting groups will be cleaved off after the formation of the final nonapeptide.

The term activated carbon acid as used hereinbefore and hereinbelow relates to a carbon acid, the carbonyl function of which has a higher activity towards amide formation than the carbon acid as such by derivation. Suitable derivates of carbon acids with higher activity towards amide formation are carboxylic acid halides, carboxylic acid azides, esters of carboxylic acids, wherein the substituted alcohol moiety functions as a leaving group, N-carboxyanhydrides and mixed carboxylic acid anhydrides.

A key step in the peptide production process is the formation of the peptide bond. In general, the following reaction scheme for amide bond formation and peptide coupling, respectively, may be applied:

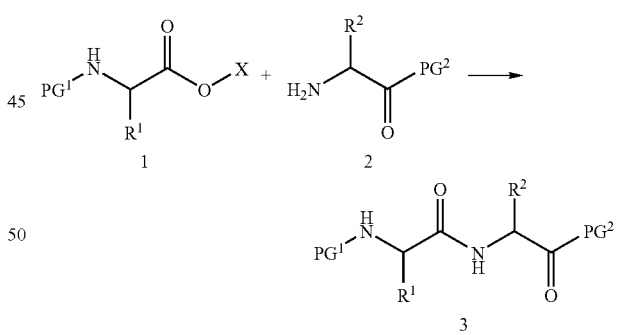

wherein $PG^1$ is a suitable amino protecting group or the corresponding N-protected N-terminal amino acid or oligopeptyl moiety of leuprolide;

$R^1$ and $R^2$ each independently are the corresponding radicals of the amino acid side chains;

$PG^2$ is a suitable carboxyl protecting group, the corresponding N-protected C-terminal oligopeptyl moiety of leuprolide or in case of the C-terminal amino acid an ethylamino group;

X is an activating moiety, which facilitates the substitution reaction at the carbonyl group.

Thereby, as an activated carboxylic acid 1, natural or synthetic amino acid building blocks may be used, whose further functional groups are either protected or do otherwise not interfere with other components present at the conditions of the coupling reaction.

Protecting groups for amino functionalities $PG^1$ are commonly known in the art. Reference is made to Philip J. Kocienski: "Protecting Groups", $3^{rd}$ Edition, Georg Thieme, Stuttgart N.Y., 2004, which gives a good overview of protecting group strategies.

Typical protecting groups for amino functionalities include, but are not restricted to acetyl (Ac), tert-butyloxycarbonyl (boc), benzyloxycarbonyl (Z), 9-fluorenylmethoxycarbonyl (fmoc), 2-(methylsulfonyl)ethoxy-carbonyl (Msc), Allyloxycarbonyl (Alloc), 1,1-dioxobenzo[b]thiophene-2-ylmethoxycarbonyl (Bsmoc) or functions of the arylsulfonyl type, such as ortho-nitrobenzenesulfonyl (o-NBS).

$R^1$ and $R^2$ of formulae 1, 2 and 3 designate any side chain of any natural or synthetic α-amino acid. In case these side chains contain functional groups, such groups are protected as known in the art of peptide synthesis, so that they do not interfere with other components present at the conditions of the coupling reaction, and further, that they are stable at the de-protection step of the amino function of the peptide for further chain elongation.

Typical side chain protecting groups include, but are not restricted to tert-butyl esters ($^tBu$), tert-butyloxycarbonyl (boc), trityl (Trt), 4-methoxy-2,3,6-phenylsulfonyl (Mtr), 2,2,5,7,8-pentamethylchroman-6-sulfonyl (Pmc), 2,2,4,6,7-pentamethyldihydrobenzo furan-5-sulfonyl (Pbf), tosyl (Tos), 4-methyltrityl (Mtt), p-methoxytrityl (Mmt), tert-butylthio ($^tButhio$), 4,4'-dimethoxybenzhydrol (Mbh), benzyl ester (OBzl), benzyl (Bzl), acetamidomethyl (Acm), β-1-adamantyl ester (o-1-Ada). Reference is made to Philip J. Kocienski: "Protecting Groups", $3^{rd}$ Edition, Georg Thieme, Stuttgart N.Y., 2004, representing a good overview on protecting group strategies for peptide synthesis.

The amine component 2 may be a natural or synthetic amino acid of which the carboxylic acid functionality and functionalities of side chains are protected or do otherwise not interfere with other components at coupling reaction conditions. Moreover, the amine component 2 may be a di- or oligopeptide consisting of natural or synthetic amino acid building blocks which are suitably protected.

$PG^2$ may designate a protecting group of the acid functionality. Typical protecting groups include, but are not restricted to methyl ester (OMe), ethyl ester (OEt), tert-butyl ($^tBu$), 3-(3-methyl-)pentyl (Mpe), 2-(2-phenyl)propyl (Pp), 2-chlortrityl (Clt), diphenyl(4-pyridyl)methyl (PyBzh), Dicyclopropylmethyl (Dcpm), 9-fourenylmethyl (Fm), 2-(trimethylsilyl)ethyl (Tmse), 4-(N-(4,4-dimethyl-2,6-dioxocyclohexylidene)-3-methylbutyl)amino)benzyl (Dmab), benzyl ester (OBzl), benzyl (Bzl) or allyl ester (OAll).

Moreover, $PG^2$ may designate at least one further α-amino acid of the peptide chain, whose other functional groups are protected in a manner so that they do not interfere with other components present at the conditions of the coupling reaction.

The activated carboxylic acid may be formed by any activation or coupling agent and coupling additive known in the field. Reference is made to So-Yeop Han, Young-Ah Kim, *Tetrahedron* 60 (2004) 2447-2467 (and references cited therein) and Peng Li, Peter P. Roller and Jiecheng Xu: *Current Organic Chemistry*, 2002, 6, 411-440 where a general overview over modern and current peptide coupling strategies is given.

As an example for an activated carboxylic acid, activated esters such as pentafluorophenyl-, pentachlorophenyl-, 4-nitrophenyl esters may be mentioned, however, any other activated ester suitable and known for peptide synthesis may also be used.

Moreover, activated carboxylic acid species such as halides, azides or N-carboxyanhydrides such as N-succinimides may be used as activated carboxylic acid.

In principle, the above-mentioned activated esters, halides, azides and N-carboxyanhydrides may also be used as pre-synthesized and isolated preactivated carboxylic acid species.

Moreover, the activated carboxylic acid may be formed in situ by the use of carboxylic acid with activating reagents alone or in combination with coupling additives. Such activating reagents and coupling additives are suited to form activated intermediates which subsequently react with the amine component.

Activating reagents include, but are not limited to carbodiimides, 1-hydroxybenzotriazole based or 1-hydroxy-7-azabenzotriazole based phosphonium and uronium salts, halouronium and halophosphonium salts, benzotriazine based uronium salts and phosphates, N-acylimidazoles and N-acyltriazoles.

As representatives for carbodiimides, N,N'-dialkylcarbodiimides such as N,N'-dicyclohexylcarbodiimide (DCC) or diisopropylcarbodiimide (DIPC) may be mentioned. Further, 1-ethyl-3-(3'-dimethylaminopropyl)-carbodiimide (EDC) may be listed.

As representatives for 1-hydroxybenzotriazole based phosphonium salts, benzotriazol-1-yl-N-oxy-tris(dimethylamino)phosphonium hexafluoro-phosphate (BOP), benzotriazol-1-yl-N-oxy-tris(pyrrolidino)phosphonium hexafluorophosphate (PyBOP) may be mentioned.

As a representative for 1-hydroxy-7-azabenzotriazole based phosphonium salts, 7-azabenzotriazol-1-yl-N-oxy-tris (pyrrolidino)phosphonium hexa-fluorophosphate (PyAOP) may be mentioned.

As representatives for 1-hydroxybenzotriazole based uronium salts, N-[(1H-benzotriazol-1-yl)(dimethylamino)methylene]-N-methylmethanami-nium hexafluorophosphate N-oxide (HBTU), N-[(1H-benzotriazol-1-yl)(dimethylamino)methylene]-N-methylmethanaminium tetrafluoroborate N-oxide (TBTU), N-[(1H-6-chlorobenzotriazol-1-yl) (dimethylamino)-methylene]-N-methylmethanaminium hexafluorophosphate N-oxide (HCTU), N-[(1H-6-chlorobenzotriazol-1-yl)(dimethylamino)methylene]-N-methyl-methanaminium tetrafluoroborate N-oxide (TCTU) may be mentioned.

As a representative for 1-hydroxy-7-azabenzotriazole based uronium salts, N-[(dimethylamino)-1H-1,2,3-triazolo [4,5-b]pyridino-aylmethylene]-N-methylmethanaminium hexafluorophosphate (HATU) may be mentioned.

As representatives for halouronium salts, bis(tetramethylene)-fluoroformamidinium hexafluorophosphate (BTFFH) and 2-chloro-1,3-dimethylimidazolidium hexafluorphosphate may be mentioned.

As representatives for halophosphonium salts, bromotris-(dimethylamino)phosphonium hexafluorophosphate (BroP), bromo-tripyrrolidino phosphonium hexafluorophosphate (PyBroP and chlorotripyrrolidino phosphonium hexafluorophosphate (PyCloP) may be mentioned.

As a representative for benzotriazine based uronium salt, O-(3,4-dihydro-4-oxo-1,2,3-benzotriazine-3-yl)-N,N,N',N'-tetramethyluronium tetrafluoro-borate (TDBTU) and 3-(diethyloxyphosphoryloxy)-1,2,3-benzotriazin-4(3H)-one (DEPBT) may be mentioned.

As a representative for benzotriazine based phosphonium salt, 3-(diethyloxyphosphoryloxy)-1,2,3-benzotriazin-4 (3H)-one (DEBPT) may be mentioned.

As a representative for an N-acylimidazole, 1,1'-carbonylbis(1H-imidazole) (CDI) may be mentioned.

As a representative for an N-acylbenzotriazole, 1,1'-carbonylbis(1H-benzotriazole) may be mentioned.

As further activating reagents, 2-bromo-1-ethyl pyridinium tetrafluoroborate (BEP, described in Peng Li, Jie-Cheng Xu: *Tetrahedron* 56 (2000) 8119-8131) and 2-chloro-4,6-dimethoxy-1,3,5-triazine (CDMT, described in Christine E. Garretts, Xinglong Jiang, Kapa Prasad, Oljan Repic: *Tetrahedron Letters* 43 (2002) 4161-4165) may be mentioned.

Coupling additives include, but are not limited to 1-hydroxybenzotriazole (HOBt), 1-hydroxy-7-azabenzotriazole (HOAt) and 3,4-dihydro-3-hydroxy-4-oxo-1,2,3-benzotriazine (HO-Dhbt).

The coupling reactions are preferably performed in the presence of a tertiary amine, which includes, but is not limited to triethylamine, ethyldiisopropylamine and N-methylmorpholine.

The peptide coupling according to the invention may be performed in inert organic solvents commonly known and used for peptide synthesis. Preferred solvents are dimethylsulfoxide, N,N-dimethylformamide, N-methylpyrrolidone, dimethylacetamide (DMAC) or mixtures thereof with further organic solvents such as dichloromethane, chloroform, 1,4-dioxane, tetrahydrofuran and ethyl acetate.

The present invention therefore provides a process for producing leuprolide whereby at least one peptide bond of the molecule is formed by reacting an activated carboxylic acid and an amine component in a continuous flow.

It has been found that when the reaction components are reacted in a continuous flow with each other, they are subjected to an efficient contact to each other during the process, thereby leading to high conversion rates.

The efficient contact results from the fact, that in continuous flow systems the reaction volume can be small, compared with the total produced output volume.

In the conventional synthesis with increasing the output volume, the vessel size has to be increased and even with constant reaction times, normally at least the adding time of reagents has to be prolonged. Due to less efficient contact of the reaction components in the case of increasing the vessel size, very often also the pure reaction time has to be prolonged.

Using continuous flow enables the control of the reaction time independently from the output volume simply by feeding raw materials longer into the reaction system. The reaction time is always determined by the ratio of reaction volume and flow rate. Increasing the concentration leads to further acceleration of the reaction, which enables to choose further shortened reaction times. By this, continuous flow yields a greatly enhanced throughput in general and when α-amino-acids are reacted, it prevents further the occurrence of epimerisation.

The continuous flow is achieved by feeding the starting materials or starting compounds simultaneously into the reaction system and by withdrawing the chemical product out of the reaction system.

Preferably, the starting materials or starting compounds and the effluent materials are fed simultaneously into and respectively out of the reaction system.

More preferred, the reaction system is completely filled with a stream of starting materials or starting compounds and a stream of effluent materials.

Preferably, the activated carboxylic acid and the amine component are fed, each in a continuous flow, simultaneously into the reaction system.

Thereby, the flow rates for each component may be the same or different from each other, depending on the concentration of the components or on their balance in the reaction.

Preferably, the activated carboxylic acid and the amine component are present in an inert liquid.

Thereby, the activated carboxylic acid and the amine component and/or the respective reaction product may form a solution, a suspension or a dispersion with the inert liquid.

As liquid, dimethylsulfoxide, N,N-dimethylformamide, N-methylpyrrolidone, dimethyl-acetamide (DMAC) or mixtures thereof with further organic solvents such as dichloromethane, chloroform, 2,2,2-trifluoroethanol, 1,4-dioxane, tetrahydrofuran and ethyl acetate are preferably used.

The efficient contact of the reaction components found for the continuous flow processes can be further improved by especially focussing on mixing.

Preferably, the activated carboxylic acid and the amine component are fed into a system bearing at least one tube or channel, wherein the components are mixed and pass through the channel, thereby forming the respective peptide bond.

Preferably, the channels have a hydraulic diameter of 50 μm to 2 mm, more preferably from 100 μm to 1.5 mm, and most preferably the channels have a hydraulic diameter of 150 μm to 1 mm.

The term hydraulic diameter indicates that various geometries of the cross-sectional area of the channel or tube may be used, i.e. the method according to the invention is independent from a specific geometry of the cross-sectional area of the channel or tube.

$$D_h = \frac{4A}{U}$$

The hydraulic diameter $D_h$ is defined as follows whereby A is the cross-sectional area and U is the wetted perimeter of the cross-section.

Preferably, the reaction system is capable of performing mixing and heat exchanging in the same device.

Preferably, mixing is achieved by diffusion. Most preferably, mixing is achieved via multi-lamination of the starting materials or starting compounds by creating alternating layers of starting materials, with a layer thickness less than the height of the channel.

It has been found that the spatial constitution or geometry of a synthesis reactor contributes to an improved reaction kinetic, i.e. due to perfect contact of each reaction component to each other, very high conversion rates are achieved in peptide coupling reactions. Thereby, the starting materials or starting compositions, namely the activated carboxylic acid and the amine component, are fed in a continuous flow into a channel preferably having a hydraulic diameter of 50 μm to 2 mm, which allows for a rapid reaction between the components with high conversion rate and essentially pure products.

The hydraulic diameter of the channel may thereby even be smaller, i.e. from 100 μm to 1.5 mm or from 150 μm to 1 mm.

The continuous flow of the starting materials into the reaction system or channel causes a continuous output of the product. Thereby, the length of the reaction channel may be varied, depending on the specific components to be reacted, in order to allow for a complete conversion to the desired product. At a given volume of the channel, the flow rate determines the residence time of the reaction mixture in the channel system.

In a further embodiment of the invention, the length of the reaction channel may be extended by a further module containing an extension channel in order to define a specific residence time of the reaction mixture in the channel system. The extension channel may have the same hydraulic diameter as given above and as used for the reaction channel.

Preferably, the process is conducted in a way that the residence time of the components or the mixture of starting material and products in the reaction channel or the reaction channel and the extension channel is less than 90 min, preferably less than 45 min, preferably less than 30 min and preferably less than 5 min, however, at least 1 sec.

Preferably, the activated carboxylic acid and the amine component are reacted in a ratio of 1.2:1 to 1:1.2, preferably in a ratio of 1.1:1 to 1:1.1, preferably from 1.05:1 to 1:1.05, and more preferably in a ratio of 1.01:1 to 1:1.01. Also, a ratio of 1:1 is possible with the effective reaction system according to the invention. Thereby, the intensive contact of the reaction partners allows for high conversion rates within short time frames.

The starting concentration of the reaction components, i.e. the carboxylic acid derivative and the amine component may be, from saturation of the reaction component in the given solvent as a highest concentration down, to 0.01 mol/l as a lowest concentration, preferably from 1.0 mol/l to 0.05 mol/l, more preferably from 0.5 mol/l to 0.1 mol/l, and most preferably from 0.3 to 0.15 mol/l.

The preferred or most preferred concentrations in combination with short reaction times allow for a high throughput and high conversion rates from starting material to product, and consequently for large scale synthesis of peptides.

The process according to the invention may be performed at any temperature known and commonly used in the field of peptide chemistry. However, temperatures from −20° C. to 60° C. are preferred. Advantageously, the temperature is kept at 20 to 60° C., and most preferably, it is kept at 30 to 50° C. Such relatively high temperature allow for a fast reaction and hence for low residence time, which is preferred for large scale synthesis. However, the process of the present invention thereby suppresses or even avoids epimerisation of the components, which would be expected to cause relevant amounts of side products at such temperatures.

In traditional peptide synthesis in a round bottom flask 3-(diethoxyphosphoryloxy)-1,2,3-benzotriazin-4(3H)-one (DEPBT) is an attractive alternate activating agent. Unfortunately, the reaction is slow and attempts to accelerate the reaction by rising the reaction temperature leads to significant epimerisation, e.g. in Pro-His-coupling reactions at −15° C. no epimerisation occurs, at 20° C. about 1-5% epimerisation is obtained and at 60° C., complete epimerisation is observed (M. Mergler, et al. (2001) J. Pept. Sci., 7, 502).

The continuous flow of the reaction partners is typically achieved via mechanical pumping or pressure. Therefore, mechanical pumps are used to build up and maintain the flow in the reaction system. As an example for mechanical pumps, piston pumps, peristaltic pumps, syringe pumps or diaphragm pumps may be mentioned. Hydrostatic and pneumatic pumps may be mentioned as an example for pressure. Thereby, hydrostatic systems may involve reservoirs with liquids that are passed through the system by their own pressure.

In principle, any transfer rate through the reaction system, and in particular through the reaction channel itself may be kept at 0.005 ml/min to 40 ml/min when concentrations as given above are used, namely from saturation of the reaction component in the given solvent as a highest concentration down to 0.01 mol/l as a lowest concentration or from 1.0 mol/l to 0.05 mol/l.

Preferably, the transfer rate through one reaction system, and in particular through the reaction channel itself may be 0.005 ml/min to 40 ml/min when the concentration of the solutions is kept at 0.1 to 0.5 mol/l.

With the assumption of a molecular weight of 300 an example for the production capacity of one reaction system is given in the following table.

TABLE I

| Production period | Transfer rate with 0.5 Mol/l | Product quantity Mol | Product quantity kg |
|---|---|---|---|
| Hour | 10 ml/min | 0.3 Mol/h | 0.09 kg/h |
| Day | 10 ml/min | 7.2 Mol/d | 2.16 kg/d |
| Year | 10 ml/min | 2400 Mol/y | 720 kg/y |
| Hour | 20 ml/min | 0.6 Mol/h | 0.18 kg/h |
| Day | 20 ml/min | 14.4 Mol/d | 4.32 kg/d |
| Year | 20 ml/min | 4800 Mol/y | 1440 kg/y |
| Hour | 40 ml/min | 1.2 Mol/h | 0.36 kg/h |
| Day | 40 ml/min | 28.8 Mol/d | 8.64 kg/d |
| Year | 40 ml/min | 9600 Mol/y | 2880 kg/y |

Preferably, the reaction channel as mentioned above forms a part of a microreactor. Further, the microreactor may be supplemented by a module for extending the residence time. Moreover, the microreactor may be supplemented with a first and/or second pre-mixer.

Moreover, more than one microreactor may be operated simultaneously, i.e. in parallel in order to achieve large scale production of leuprolide, in particular industrial scale production. The advantage of using an assembly of parallel operated microreactors is to avoid time consuming scale-up of reactions, but rather use a numbering up of already optimized reaction processes. Another advantage is the easier control of reaction temperature and reaction time of the process.

Preferably, the activated carboxylic acid according to the process of the invention is formed by reaction of a carboxylic acid and an activating agent. Thereby, the activating agent may contain or comprise a coupling agent.

Preferably, the process according to the present invention comprises a premixing step prior to the formation of the amide bond.

Thereby, a carboxylic acid and an activating agent are mixed in a first pre-mixer. It has been surprisingly found that when a premixing step is involved, the racemization or epimerisation in peptide bond forming may further be effectively suppressed or avoided.

It is preferred that the stagnant volume in the pre-mixer is kept as small as possible. Thereby the pre-mixer may consist of any equipment capable to mix two or more liquids. For instance, the pre-mixer may consist of a T-piece. T-pieces are commonly used in chemistry, for instance in HPLC techniques. For the present invention, 1/16" T-pieces may preferably be used. On the other hand, the pre-mixer may also consist of a microreactor.

Preferably, the carboxylic acid and the activating agent are fed in a continuous flow and separately from each other via inlet channels into a first pre-mixer equipped with a mixing channel where the mixing essentially takes place.

If desired, a coupling additive may be added to the activating agent.

Thereby, the activated carboxylic acid may be formed in the mixing channel of the first pre-mixer. Alternatively, it may be in situ formed in the reaction channel subsequent to the mixing channel of the first pre-mixer.

Alternatively, an activated carboxylic acid and a coupling additive may be mixed in a first pre-mixer. Again, the pre-mixer comprises inlet channels and a mixing channel.

Preferably, the first pre-mixer is located directly before the reaction channel so that the mixing of carboxylic acid with activating agent and activating agent together with coupling additive, respectively, is achieved instantaneously before the peptide coupling itself. Thereby, instantaneously is meant in a timely and spatial manner.

Moreover, prior to the formation of the peptide bond, the amine component and a base may be mixed in a second pre-mixer. Preferably, the amine component and the base are fed in a continuous flow and separately from each other via inlet channels into a second pre-mixer equipped with a mixing channel where the mixing essentially takes place.

Again, the second pre-mixer is preferably located directly before the reaction system where peptide coupling takes place.

For the premixing, the carboxylic acid, the activating agent, the coupling additive, the amine component and the case may be fed into the respective pre-mixers in form of a solution, a suspension or a dispersion.

The work up of the produced peptides is effected by leading the continuous flow of product into an aqueous solution of NaCl, for instance at a concentration of 5 wt %. Alternatively, water or any other common buffer may be used.

Subsequently, the collected product suspension is extracted with organic solvent which is immiscible with water. Preferably, organic solvents such as ethyl acetate, dichloromethane or methyl-tert-butyl ether are used. The organic phases may then be re-extracted with aqueous solution of salt, preferably NaCl, NaHCO$_3$, Na$_2$CO$_3$ or citric acid. After drying the organic phase with commonly known drying agents, preferably with MgSO$_4$ or Na$_2$SO$_4$, the resulting peptide is separated from the solvent, preferably by evaporation of the solvent under reduced pressure.

Usually, no further purification step such as chromatographic purification is necessary as the process according to the invention allows for the production of essentially pure products.

The peptide synthesis is then followed by a subsequent deprotection step of either the protected amine or the acid functionality. Respective deprotection methods are known in the field. Reference is made to Philip J. Kocienski: "Protecting Groups", 3$^{rd}$ Edition, Georg Thieme, Stuttgart N.Y., 2004 and references cited therein. Deprotection may either be performed by reacting the protected peptide with deprotecting reagent in a continuous flow. Preferably, the protected peptide and the deprotecting reagent are fed, each in a continuous flow, simultaneously into the reaction system. Preferably, both, the protected peptide and the deprotecting reagent, respectively, are present in an inert liquid, thereby forming a solution, a suspension or a dispersion. The reaction system may be the same as described above.

Alternatively, the deprotection step may be performed in a batch reaction, i.e. in a commonly used reaction vessel such as glass equipment at a size ranging from 250 ml to 100 l. For deprotection of the tert-butyloxycarbonyl (boc) protecting group, formic acid is preferably used.

Various protecting and synthesis strategies for the build-up of leuprolide may be chosen, as commonly known in the field. Reference is made to DE 2446005C2 or U.S. Pat. No. 3,914,412.

Preferably, the following side chain protecting strategy is applied: 5-Oxoproline is protected by acylation of the amide functionality, histidine is protected by alkylation of the aromatic amine functionality, thyrosine is protected by alkylation of the phenolic alcohol functionality, tryptophane is protected by acylation of the aromatic amine functionality, serine is protected by alkylation of the hydroxyl functionality, arginine is preferably protected with arylsulfonyl protecting derivatives.

Further, leuprolide may be synthesized by subsequent condensation of one amine component after the other onto the growing chain. Moreover, a synthesis strategy may be applied where dipeptide and tripeptide building blocks, respectively, are reacted with each other to give small peptide chains of four to six amino acids. This so-called block condensation may be further used for the synthesis of peptide chains with seven, eight or nine amino acids, in order to finally obtain the protected leuprolide intermediate.

In a preferred embodiment of the process according to the invention leuprolide and/or the intermediate oligopetides thereof are prepared by a process which comprises the steps of:

(a) reacting an N-protected amino acid or oligopeptide of formula (I), $$(Xaa_i)_n\text{-CO-L} \quad (I)$$

wherein

Xaa$_i$ represents an N-protected amino acid moiety at the position i, which position within the leuprolide chain is equal to index n;

n is an integer of 1 to 8, preferably 3, 4 or 5, most preferably 5;

L is a suitable leaving group, which enhances the activity of the carboxyl group towards amide formation in comparison with a hydroxyl group;

with a amino acid or oligopeptide of formula (II), $$H_2N\text{-}(Xaa_i)_{m-n}\text{-CO—NHC}_2H_5 \quad (II)$$

wherein

Xaa$_i$ represents an amino acid moiety at the position (i=m-n), wherein all amino groups of the amino acid moieties with the exception of the N-terminal amino acid of formula (II) are protected by a suitable amino protecting group;

m is an integer of 2 to 9, preferably an integer of 4 to 9, most preferably 5 or 9;

in a continuous flow; and (b) cleaving off the protecting groups.

The meaning of the different N-protected amino acid moieties is indicated in the following table II:

TABLE II

| n | Xaa$_i$ |
|---|---|
| 1 | Pyr |
| 2 | His |
| 3 | Trp |
| 4 | Ser |
| 5 | Tyr |
| 6 | Leu |
| 7 | Leu |
| 8 | Arg |

Final deprotection may be achieved by deprotecting steps commonly known in the field. Reference is made to Peng Li, Peter P. Roller and Jiecheng Xu: *Current Organic Chemistry*, 2002, 6, 411-440. Preferably, a mixture of trifluoro acetic acid (in most cases diluted with dichloromethane) in the presence of scavenging reagents like thioanisol, DTT (dithiothreitol) is used.

In a final step, the acetate salt of leuprolide is produced according to a procedure cited in patent application DE 24 46 005 C2.

In the following examples, the principle of the inventive will be shown by a synthesis of a nonapeptide.

Equipment

For all reactions a CYTOS® Lab System (CPC-Systems GmbH, Mainz, Germany) equipped with a CYTOS® microreactor, additional residence time units in order to realize suitable residence times (see experimental details) and a thermostating unit (Huber) was used. Two syringe pumps devices equipped with two 10 ml syringes each (Kloehn) were used for feeding the raw materials in the reactor.

Conventional $\frac{1}{16}$" T-pieces (junction) as used for HPLC systems and an additional pump were chosen for achieving the premixing, if necessary. The syringe pumps maybe replaced by rotary piston pumps (Ismatec).

Analytics

All reactions were monitored by HPLC using a HP 1100 (Hewlett-Packard) system, equipped with a UV detector capable of monitoring at 205 nm, an injector capable to inject 20 µL and suitable integrating device. For the whole synthesis sequence a linear gradient was run according the following scheme:

| Column: | Xterra RP18 5 µm, 4.6 × 250 mm | |
|---|---|---|
| Eluent: | A = 0.1% TFA in water - B = 0.1% in acetonitrile | |
| Flow: | 1.5 ml/min | |
| Gradient: | 0 min | 8% B |
| | 10 min | 65% B |
| | 16 min | 100% B |
| | 18 min | 100% B |
| | 18.01 min | 8% B |
| | 23 min | 8% B |

General Procedure for HBTU Promoted Coupling

All materials required for the reaction are dissolved in anhydrous DMF or DMAC. A total of four storage containers which are kept under argon, are individually filled with the acid component used, HBTU as coupling reagent, the amino compound and triethylamine (DIPEA in case of Fmoc protecting groups present in the coupling compounds). Concentrations are preferably in the range of about 0.2 mol/l and the CYTOS® Lab System is set to the suitable reaction temperature by the external thermostating unit. The pumps are initialised and the system is filled with the appropriate solvent (DMAC or DMF) from a separate vessel. After the system is filled with DMF (peptide grade), the containers with the starting material solutions are fitted with the system and the premixed solutions (A+B) and (C+D) fed into the reactor by separate inlet pipes using flow rates required to achieve the appropriate residence times. A well stirred vessel with 5% sodium chloride solution cooled with an ice bath is used for product collection. At 1.5 τ a sample for IPC by HPLC is taken in order to determine a) if the steady state of the system has been reached and b) if the reaction shows the appropriate turnover. If needed, the pumps are calibrated again. After having consumed all starting materials the inlet feed is switched to solvent (dry DMAC or DMF) and product collection is continued for further 1.5 inner system volumes of reaction mixture. Then the product valve is switched to waste and the system is cleaned with solvent followed by water and ethanol.

The collected product suspension is extracted with a mixture of ethyl acetate and MTBE for two or three times. The combined organic layers are washed with 0.5 M citric acid (pH control), then with 5% sodium chloride solution, 10% NaHCO$_3$ solution, again with 5% sodium chloride solution and finally with concentrated brine. After drying the combined organic phases over MgSO$_4$ the solvent is removed under reduced pressure (bath temperature max. 30° C.) yielding the crude product. The content (yield) of the product is determined by HPLC analysis.

General Procedure for Boc-Cleavage

The crude material of the coupling step is dissolved in cold formic acid and stirred under argon-atmosphere at room temperature unto completion (HPLC control). Subsequently, the formic acid is removed at 35° C. under reduced pressure. To ensure the complete removal of the acid the residue is co-evaporated several times with toluene and evaporated to dryness. Finally desalting is achieved using a DOWEX 1-X8 ion exchange resin.

General Procedure for Fmoc-Cleavage

In an appropriate round bottomed flask equipped with a dropping funnel the peptide is dissolved in ethyl acetate and cooled to 0° C. A solution of 1.5 equivalents of TAEA (tris aminoethyl amine) in ethyl acetate is added dropwise and the mixture stirred for additional 30 min unto completion of the reaction. The tenfold amount of ethyl acetate is added and the slurry treated in an ultrasonic bath for 5 min. The precipitate is filtered off and the filtrate extracted four times with 5% sodium chloride solution and additionally with concentrated brine. After drying over 30 g of magnesium sulfate the solvent is evaporated (at 20° C.) to a small volume of ~30 ml. The product content is determined by HPLC. The solution is directly used in the next coupling step.

General Procedure for Saponification

A 0.6 M solution of crude ester in ethanol is cooled down to 0° C. and a solution of 10 equivalents of 10N NaOH in water is added drop wise and the mixture is stirred for 2 h or unto completion of the reaction. 2/3 parts of the ethanol are removed under reduced pressure at 30° C. and dichloro methane is added followed by 1 M citric acid. The phases are separated and the aqueous layer is extracted twice with dichloro methane. The combined organic layers are washed with 5% sodium chloride solution and with 100 ml of conc. brine. After drying with MgSO$_4$ the solvent is removed under reduced pressure and the residue is dried in vacuum.

Boc-Arg(Mtr)-Pro-NHEt

According to the general procedure for HBTU promoted coupling solutions of 31.5 g Boc-Arg(Mtr)-OH in DMAC, 24.79 g HBTU in DMAC, 11.56 g H-Pro-NHEt.HCl in DMAC and 19.60 g triethylamine in DMAC were premixed and fed into the reactor at 50° C. using a residence time of 1.1 min to yield 52 g crude material which was used in the next step without purification. The calculated yield from HPLC analysis was 99%.

Arg(Mtr)-Pro-NHEt.HCOOH

According to the general procedure for Boc-cleavage 52 g Boc-Arg(Mtr)-Pro-NHEt (0.38 M in DMAC) were treated with 250 ml formic acid to yield 39 g product (90% yield based on HPLC analysis) as formiate. Finally the material was desalted using a Dowex 1-X8 ion exchange resin. Boc-D-Leu-Leu-OAllyl According to the general setup of coupling reactions a solution of 21.03 g of Boc-D-Leu-OSu in 126 ml of dry DMF and a solution of 22.0 g H-Leu-OAll.HOTos and 19.4 g triethylamine in 128 ml dry DMF was fed into the microreactor at 50° C. using a CYTOS® Lab System equipped with two additional residence time units (15 ml each) at 60° C. using a total flow of 3.2 ml/min resulting in a residence time of 10 min. The product was collected and isolated as usual to yield 22.9 g of crude product which was used in the next reaction without purification.

According to the general saponification procedure, 6.11 g crude Boc-D-Leu-Leu-OAllyl were saponified with 3 g sodium hydroxide in ethanol/water to yield 5.0 g crude Boc-D-Leu-Leu-OH which was used in the next step without purification Boc-D-Leu-Leu-Arg(Mtr)-Pro-NHEt (SEQ ID NO: 2)

According to the general procedure for HBTU pro-moted coupling, 14.0 g Boc-D-Leu-Leu-OH, 20.7 g Arg (Mtr)-Pro-NHEt, 16.6 g HBTU, 9.3 ml triethylamine were premixed and reacted in a CYTOS® Lab System in anhy-drous DMF at 40° C. and a residence time of 2 min at a total flow rate of 23.5 ml/min to yield 18.2 g crude material (yield based on HPLC analysis: 60%) which was used in the next step without purification.

D-Leu-Leu-Arg(Mtr)-Pro-NHEt (SEQ ID NO: 3)

According to general procedure for BOC-cleavage, 500 mg crude Boc-D-Leu-Leu-Arg(Mtr)-Pro-NHEt was treated with 2 ml formic acid yielding 350 mg crude D-Leu-Leu-Arg(Mtr)-Pro-NHEt (yield based on HPLC: 80%).

Pyr-His(Trt)-OMe

According to the general procedure for HBTU promoted coupling, 4.7 g (10.5 mmol) H-His(Trt)-OMe.HCl, 4.54 g (10.8 mmol) HBTU, 2.69 g (10.5 mmol) Pyr-OH and 8.3 ml (26.3 mmol) DIPEA were reacted in a CYTOS® Lab System in anhydrous DMF at total flow of 26.7 ml/min and a residence time of 1.2 min to yield 5.3 g of crude Pyr-His(Trt)-OH which was used in the next step without purification. Yield based on HPLC: 81%.

Pyr-His(Trt)-OH

According to the general procedure for saponification, 5.6 g crude Pyr-His(Trt)-OMe were treated with 3.6 g sodium hydroxide in ethanol/water yielding 5.6 g of crude material (yield based on HPLC: 99%)

Fmoc-Ser($^t$Bu)-Tyr($^t$Bu)-OAllyl

According to the general procedure for HBTU promoted coupling, 18.26 g Fmoc-Ser(tBu), 16.95 g HBTU, 11.95 g H-Tyr(tBu)-OAllyl and 26.10 ml DIPEA were reacted in a CYTOS® Lab System in anhydrous DMF at 45° C. and at a total flow rate of 32 ml/min at residence time of 1 min to yield 26.09 g crude material (yield based on HPLC: 96%) which was used in the next step without purification.

Ser($^t$Bu)-Tyr($^t$Bu)-OAllyl

According to the general procedure for Fmoc-cleavage, 9 g Fmoc-Ser($^t$Bu)-Tyr($^t$Bu)-OMe, 22 ml TAEA in ethyl acetate yielded 4.7 g of crude product (yield based on HPLC: 88%).

Fmoc-Trp(boc)-Ser($^t$Bu)-Tyr($^t$Bu)-OAllyl

According to the general procedure for HBTU promoted coupling, crude H-Ser($^t$Bu)-Tyr($^t$Bu)-OAllyl, freshly Fmoc-cleavaged from 33.3 g of Fmoc-Ser($^t$Bu)-Tyr($^t$Bu)-OAllyl were reacted in a CYTOS® Lab System with 27.3 g of Fmoc-Trp(boc)-OH, 20.15 g HBTU and 17.7 ml of DIPEA in anhydrous DMF yielding 49.2 g crude product (yield based on HPLC: 91%).

49.2 g of crude Fmoc-Trp(boc)-Ser(Bu)-Tyr($^t$Bu)-OAllyl were treated with 9.2 ml of TAEA as described in the general procedure for Fmoc-cleavage, yielding 45.3 g of crude product (yield based on HPLC: 98%), which is subse-quently used for the next coupling.

Pyr-His (Trt)-Trp(boc)-Ser($^1$Bu)-Tyr($^t$Bu)-Oallyl (SEQ ID NO: 4)

Solutions of 45.3 g of crude Trp(boc)-Ser($^t$Bu)-Tyr ($^t$Bu)-OAllyl in 80 ml of anhydrous DMF, and 22.0 g of Pyr-His (Trt)-OH in 120 ml of anhydrous DMF are prepared and combined in a vessel. After cooling to -15° C. a solution of 14.86 g of DEPBT and 9.34 g of HOBT.H$_2$O in 50 ml of anhydrous DMF is added and stirred for additional 15 min Finally, a solution of 10.5 ml DIPEA in 10 ml of anhydrous DMF is added and the mixture stirred for 12 hrs at 15° C. After workup similar to the description in the general coupling procedure, 49.16 g crude material are obtained. The calculated yield from HPLC analysis was 78%.

Pyr-His (Trt)-Trp(boc)-Ser($^t$Bu)-Tyr($^t$Bu)-OH (SEQ ID NO: 4)

According to the general saponification procedure, 6.34 g crude Pyr-His(Trt)-Trp(boc)-Ser($^t$Bu)-Tyr($^t$Bu)-OAllyl were saponified with 10.8 ml of 1 M sodium hydroxide in ethanol/water. After aqueous work up, the crude product is redissolved in dichloro methan and MTBE is added. The precipitate is filtered off and dried in vacuum, yielding 5.95 g of Pyr-His(Trt)-Trp(boc)-Ser($^t$Bu)-Tyr($^t$Bu)-OH (yield based on HPLC: 94%)

Pyr-His (Trt)-Trp(boc)-Ser($^t$Bu)-Tyr($^t$Bu)-D-Leu-Leu-Arg (Mtr)-Pro-NHEt (SEQ ID NO: 5)

According to the general procedure for HBTU promoted coupling, 7.43 g of crude D-Leu-Leu-Arg(Mtr)-Pro-NHEt were reacted in a CYTOS® Lab System with 11.64 g of Pyr-His(Trt)-Trp(boc)-Ser($^t$Bu)-Tyr($^t$Bu) and 3.25 ml of DIPEA.

Differing from the general procedure, 7.41 g of PyBOP and 1.92 g of HOBT are used for the reaction instead of HBTU. For the reaction a temperature of 35° C. and a residence time of 40 min at a total flow rate of 3 ml/min is adjusted. After aqueous work up, 19.7 g of crude Pyr-His (Trt)-Trp (boc)-Ser ($^t$Bh)-Tyr($^t$Bu)-D-Leu-Leu-Arg(Mtr)-Pro-NHEt are isolated. The calculated yield from HPLC analysis was 68%.

Pyr-His-Trp-Ser-Tyr-D-Leu-Leu-Arg-Pro-NHEt (SEQ ID NO: 5)

14 g of crude Pyr-His(Trt)-Trp(boc)-Ser(tBu)-Tyr(tBu)-D-Leu-Arg(Mtr)-Pro-NHEt are dissolved in 60 ml of dichloro methan and 17 g of DTT are added, followed by 150 ml of TFA. The mixture is stirred under reflux for 6 h and then the solution is poured into 450 ml of MTBE. The precipitate is filtered, redissolved in water and purified by chromatography using carboxymethyl cellulose and a gradient of water and 0.2 M aqueous ammonium acetate solution as eluent. 7.1 g of product is isolated with a calculated yield from HPLC analysis of 59%.

The invention claimed is:

1. A process comprising:
   producing the nonapeptide leuprolide or an N-protected intermediate oligopeptide thereof of formula 5-oxo-L-prolyl-L-histidyl-L-tryptophyl-L-seryl-L-tyrosyl (SEQ ID NO: 6), by:
   forming at least one peptide bond of the compound by reacting an activated carboxylic acid and an amine component in a continuous flow, and
   feeding said activated carboxylic acid and said amine component, each in a continuous flow, simultaneously into a reaction system.

2. The process according to claim 1, wherein the activated carboxylic acid and the amine component are fed into a system bearing at least one channel, wherein mixing and passing the components through the system bearing the at least one channel forms the respective amide bond.

3. The process according to claim 2, wherein the channel has a hydraulic diameter of 50 μm to 2 mm.

4. The process according to claim 2, characterized in that the reaction channel is extended by a further module containing an extension channel.

5. The process according to claim 1, wherein the activated carboxylic acid and the amine component are reacted in a ratio of 1.2:1 to 1:1.2.

6. The process according to claim 2, wherein the channel is part of a microreactor.

7. The process according to claim 6, wherein more than one microreactors are operated in parallel.

8. The process according to claim 1, wherein the activated carboxylic acid is formed by reacting a carboxylic acid and an activating agent.

9. The process according to claim 8, wherein the activating agent contains a coupling agent selected from the group consisting of 1-hydroxybenzotriazole, 1-hydroxy-7-azabenzotriazole and 3,4-dihydro-3-hydroxy-4-oxo-1,2,3-benzotriazine.

10. The process according to claim 1, wherein prior to the formation of the peptide bond, feeding a carboxylic acid and an activating agent in a continuous flow and, separately from each other, via inlet channels into a first pre-mixer equipped with a mixing channel where the mixing essentially takes place.

11. The process according to claim 10, wherein the mixing channel is part of a microreactor.

12. The process according to claim 1, wherein prior to the formation of the peptide bond, feeding an activated carboxylic acid and a coupling agent in a continuous flow and, separately from each other, via inlet channels into a pre-mixer equipped with a mixing channel where the mixing essentially takes place; and
   wherein the coupling agent selected from the group consisting of 1-hydroxybenzotriazole, 1-hydroxy-7-azabenzotriazole and 3,4-dihydro-3-hydroxy-4-oxo-1,2,3-benzotriazine.

13. The process according to claim 12, wherein the mixing channel is part of a microreactor.

14. The process according to claim 1, wherein prior to the formation of the amide bond, feeding the amine component and a base in a continuous flow and, separately from each other, via inlet channels into a second pre-mixer equipped with a mixing channel where the mixing essentially takes place.

15. The process according to claim 14, wherein the mixing channel is part of a microreactor.

16. The process according to claim 1, wherein prior to the formation of the peptide bond,
   (a) feeding an activated carboxylic acid and a coupling agent in a continuous flow and, separately from each other, via inlet channels into a first pre-mixer equipped with a mixing channel where the mixing essentially takes place; and
   (b) feeding the amine component and a base in a continuous flow and, separately from each other, via inlet channels into a second pre-mixer equipped with a mixing channel where the mixing essentially takes place.

17. The process according to claim 16, wherein the mixing channels of the first and the second pre-mixer are part of one single microreactor or of two separate microreactors.

18. The process according to claim 16, wherein the coupling agent is selected from the group consisting of 1-hydroxybenzotriazole, 1-hydroxy-7-azabenzotriazole and 3,4-dihydro-3-hydroxy-4-oxo-1,2,3-benzotriazine.

* * * * *

SEQUENCE LISTING

<160> NUMBER OF SEQ ID NOS: 6

<210> SEQ ID NO 1
<211> LENGTH: 9
<212> TYPE: PRT
<213> ORGANISM: Artificial Sequence

```
<220> FEATURE:
<223> OTHER INFORMATION: synthetic peptide

<400> SEQUENCE: 1

Pro His Trp Ser Thr Leu Leu Arg Pro
1               5

<210> SEQ ID NO 2
<211> LENGTH: 4
<212> TYPE: PRT
<213> ORGANISM: Artificial Sequence
<220> FEATURE:
<223> OTHER INFORMATION: synthetic peptide

<400> SEQUENCE: 2

Leu Leu Arg Pro
1

<210> SEQ ID NO 3
<211> LENGTH: 4
<212> TYPE: PRT
<213> ORGANISM: Artificial Sequence
<220> FEATURE:
<223> OTHER INFORMATION: synthetic peptide

<400> SEQUENCE: 3

Leu Leu Arg Pro
1

<210> SEQ ID NO 4
<211> LENGTH: 4
<212> TYPE: PRT
<213> ORGANISM: Artificial Sequence
<220> FEATURE:
<223> OTHER INFORMATION: synthetic peptide

<400> SEQUENCE: 4

His Trp Ser Tyr
1

<210> SEQ ID NO 5
<211> LENGTH: 8
<212> TYPE: PRT
<213> ORGANISM: Artificial Sequence
<220> FEATURE:
<223> OTHER INFORMATION: synthetic peptide

<400> SEQUENCE: 5

His Trp Ser Tyr Leu Leu Arg Pro
1               5

<210> SEQ ID NO 6
<211> LENGTH: 5
<212> TYPE: PRT
<213> ORGANISM: Artificial Sequence
<220> FEATURE:
<223> OTHER INFORMATION: synthetic peptide

<400> SEQUENCE: 6

Pro His Trp Ser Tyr
1               5
```